US00PP23388P3

(12) United States Plant Patent

Klemm et al.

(10) Patent No.: US PP23,388 P3

(45) Date of Patent: Feb. 12, 2013

(54) *OSTEOSPERMUM* PLANT NAMED 'KLEOE10179'

(50) Latin Name: *Osteospermum ecklonis* Norl.
Varietal Denomination: KLEOE10179

(75) Inventors: Nils Klemm, Stuttgart (DE); Andrea Dohm, Pforzheim (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 19 days.

(21) Appl. No.: 13/135,448

(22) Filed: Jul. 6, 2011

(65) Prior Publication Data

US 2013/0014302 P1 Jan. 10, 2013

(51) Int. Cl.
*A01H 5/00* (2006.01)

(52) U.S. Cl. ..... Plt./360

(58) Field of Classification Search ..... Plt./360
See application file for complete search history.

*Primary Examiner* — Susan McCormick Ewoldt

(74) *Attorney, Agent, or Firm* — Jondle & Associates, P.C.

(57) ABSTRACT

An *Osteospermum* variety named 'KLEOE10179'; particularly distinguished by a stable uniformly enlarged disc floret corolla and a compact growth habit is disclosed.

1 Drawing Sheet

Genus and species: *Osteospermum ecklonis* Norl.
Variety denomination: 'KLEOE10179'.

BACKGROUND OF THE NEW PLANT

The present invention comprises a new and distinct variety of *Osteospermum* plant, botanically known as *Osteospermum ecklonis* Norl., and hereinafter referred to by the variety name 'KLEOE10179'. The new variety originated from a controlled cross conducted in June 2007 in Stuttgart, Germany. The female parent was a proprietary *Osteospermum* plant named 'Mutant 1' (unpatented), and the male parent was a proprietary *Osteospermum* plant named 'V 78' (unpatented). A single plant selection was subsequently chosen for further evaluation and for asexual propagation.

The new variety was first propagated via vegetative cuttings in April 2008 in Stuttgart, Germany and has been asexually reproduced repeatedly by vegetative cuttings over three to four generations. The present invention has been found to retain its distinctive characteristics through successive asexual propagations via vegetative cuttings.

Plant Breeder's Rights for this variety were applied for in Norway on Sep. 29, 2010, Switzerland on Sep. 20, 2010, European Union on Sep. 29, 2010, and Canada on Feb. 15, 2011. 'KLEOE10179' has not been made publicly available or sold more than one year prior to the filing date of this application.

SUMMARY OF THE INVENTION

The following are the most outstanding and distinguishing characteristics of the new variety when grown under normal horticultural practices in Stuttgart, Germany.

1. Stable uniformly enlarged disc floret corolla; and
2. Compact growth habit.

DESCRIPTION OF THE PHOTOGRAPH

This new *Osteospermum* plant is illustrated by the accompanying photograph which shows a whole plant, including the blooms, buds, and foliage. The colors shown are as true as can be reasonably obtained by conventional photographic procedures. The photograph was taken in Summer 2010 of a 7-month old plant in the field in Stuttgart, Germany, under conditions which approximate those generally used in normal horticultural practice.

DESCRIPTION OF THE NEW VARIETY

The following detailed descriptions set forth the distinctive characteristics of 'KLEOE10179'. The data which define these characteristics were collected from asexual reproductions carried out in Stuttgart, Germany. The plant history was taken in the Summer of 2010 on 7-month old plants which were potted at 4 weeks in 12 centimeter containers and then planted in the ground in May 2010. The plants were pinched once at 6 weeks. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:

*Family*.—Asteraceae.
*Botanical name*.—*Osteospermum ecklonis* Norl.
*Common name*.—African daisy.

Plant:

*Form and habit*.—Herbaceous perennial but usually cultivated as an annual.
*Growth habit*.—Upright.
*Branching habit*.—Freely branching.
*Height (from top of soil, including inflorescence)*.—28.0 cm.
*Width (including inflorescences)*.—27.0 cm.
*Propagation*.—Vegetative cuttings.
*Time to produce a finished flowering plant*.—Approximately 14 weeks.
*Time to initiate and develop roots*.—Approximately 3 weeks.
*Root description*.—Freely rooting.

Leaves:
*Arrangement*.—Arranged in a whorl.
*Shape*.—Dentiform.
*Apex*.—Obtuse.
*Base*.—Acute.
*Margin*.—Deeply serrate.
*Color*.—Immature leaf: Upper surface: RHS 137A. Lower surface: RHS 137C. Mature leaf: Upper surface: RHS N137C. Lower surface: RHS 137C.
*Length*.—5.2 cm.
*Width*.—1.9 cm to 2.0 cm.
*Texture*.—Leathery.
*Petioles*.—Absent.

Stems:
*Total number of branches at base of plant*.—7 to 8 (calculated at the base of the plant).
*Length*.—28.0 cm.
*Diameter*.—5.0 mm.
*Internode length*.—Approximately 1.0 cm.
*Color*.—RHS 138A.
*Texture*.—Rough.

Inflorescence buds:
*Shape*.—Obovate.
*Length*.—1.1 cm.
*Diameter*.—8.0 mm.
*Color* (*at tight bud just before the ray florets unfold*).—RHS 137A.

Inflorescence:
*Type*.—Single.
*Blooming habit*.—Spring to Fall.
*Quantity of inflorescences per plant*.—25.
*Lastingness of the inflorescences on the plant*.—10 to 14 days.
*Fragrance*.—Absent.
*Inflorescence diameter*.—4.2 cm.
*Disc diameter*.—2.5 cm.

Disc florets:
*Quantity per inflorescence*.—70.
*Shape*.—Oblanceolate.
*Tube color*.—Closed: RHS 76B. Mature: RHS 76C.
*Length*.—1.0 to 1.9 mm.
*Diameter* (*at apex*).—2.0 mm.
*Apex*.—Obtuse.
*Apex color*.—RHS 182C.
*Base*.—Acute.
*Margin*.—Entire.

Ray florets:
*Quantity per inflorescence*.—17 to 18.
*Shape*.—Oblanceolate.
*Color*.—Upper surface: RHS N155A. Lower surface: RHS 76A.
*Length*.—2.6 cm.
*Width*.—7.0 mm to 8.0 mm.
*Apex*.—Obtuse.
*Base*.—Acute.
*Margin*.—Entire.
*Texture*.—Smooth.

Peduncle:
*Length*.—6.0 cm to 7.0 cm.
*Diameter*.—2.0 mm.
*Texture*.—Rough.
*Color*.—RHS N134C.

Phyllaries:
*Arrangement*.—Single.
*Observed quantity per plant*.—16.
*Shape*.—Lanceolate.
*Color*.—Upper surface: RHS 137B. Lower surface: RHS 132A.
*Length*.—1.0 cm.
*Width*.—1.2 mm.
*Apex*.—Acute.
*Base*.—Obtuse.
*Margin*.—Entire.
*Texture*.—Rough.

Reproductive organs:
*Androecium*.—Location: Located at the base of the disc floret corolla. Stamens: Quantity: 70. Shape: Filamentous. Color: RHS 72B. Filament length: 4.5 mm. Filament diameter: 0.2 mm. Anther: Shape: Elliptic. Color: RHS N79A. Length: 1.2 mm. Diameter: 0.5 mm. Pollen: Color: RHS 22B. Amount: Sparse.
*Gynoecium*.—Location: Located at the base of the ray florets; pistils in disc florets are degenerated and nonfunctional. Pistils: Number: 17. Length: 7.0 mm. Diameter: 1.0 mm. Stigma: Color: RHS N79A. Shape: Bipartite. Length: 1.2 mm. Diameter: 0.1 mm. Style: Color: RHS 76B. Length: 2.1 mm. Diameter: 0.1 mm. Shape: Elliptic.

Fruit and seed set: Seed set was observed.

COMPARISON WITH PARENTAL, SIBLING AND COMMERCIAL VARIETIES

'KLEOE10179' differs from the female parent, the proprietary *Osteospermum* plant named 'Mutant 1' in that 'KLEOE10179' has white flowers, while 'Mutant 1' has pink-purple flowers. Additionally, 'KLEOE10179' has a stable uniformly enlarged disc floret corolla, while 'Mutant 1' has a partially enlarged disc floret corolla. Lastly, 'KLEOE10179' has a compact growth habit, while 'Mutant 1' has a medium vigorous growth habit.

'KLEOE10179' differs from the male parent, the proprietary *Osteospermum* plant named 'V 78' in that 'KLEOE10179' has a stable uniformly enlarged disc floret corolla, while 'V 78' has a normal disc floret corolla.

'KLEOE10179' differs from the sibling *Osteospermum* plant named 'KLEOE10181' (Co-pending U.S. Plant patent application Ser. No. 13/135,457) in that 'KLEOE10179' has an upright growth habit, a ray floret lower surface color of RHS 76A, and a disc floret quantity of 70, whereas 'KLEOE10181' has a semi-upright growth habit, a ray floret lower surface color of RHS 82A, and a disc floret quantity of approximately 120.

There are no available commercial varieties that are comparable to 'KLEOE10179'.

We claim:

1. A new and distinct variety of *Osteospermum* plant named 'KLEOE10179' as shown and described herein.

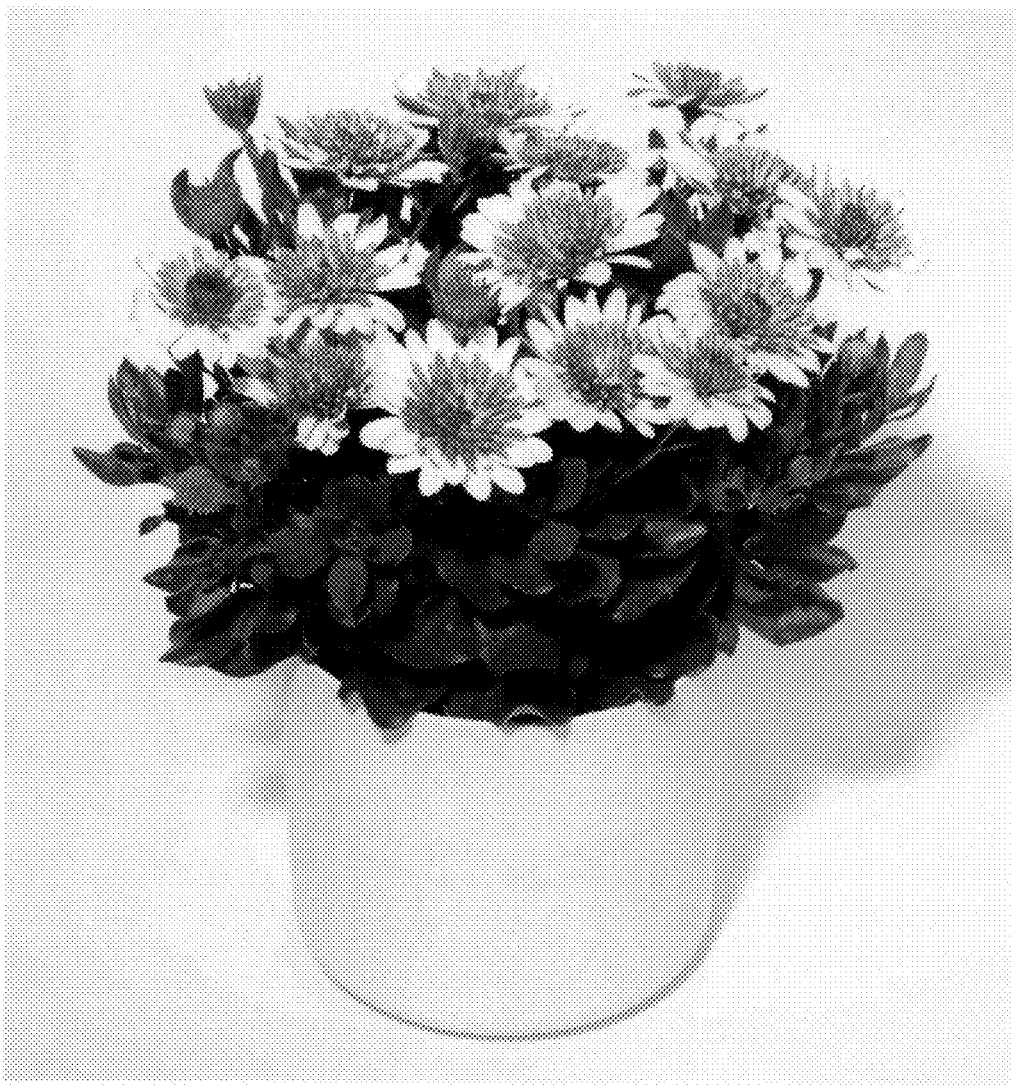

* * * * *